US00PP37593P2

(12) United States Plant Patent
Byrne et al.

(10) Patent No.: US PP37,593 P2
(45) Date of Patent: Aug. 18, 2026

(54) PEACH TREE NAMED 'TRHIC104LW'

(50) Latin Name: *Prunus persica*
Varietal Denomination: TRHIC104LW

(71) Applicant: The Texas A&M University System, College Station, TX (US)

(72) Inventors: David H. Byrne, Bryan, TX (US); Natalie Anderson, Calvert, TX (US)

(73) Assignee: The Texas A&M University System, College Station, TX (US)

( * ) Notice: Subject to any disclaimer, the term of this patent is extended or adjusted under 35 U.S.C. 154(b) by 0 days.

(21) Appl. No.: 19/336,375

(22) Filed: Sep. 22, 2025

(51) Int. Cl.
*A01H 5/08* (2018.01)

(52) U.S. Cl.
USPC ..... Plt./195

(58) Field of Classification Search
USPC ..... Plt./156, 180, 194, 195
See application file for complete search history.

(56) References Cited

U.S. PATENT DOCUMENTS

PP14,629 P3 3/2004 Byrne et al.
PP26,119 P3 11/2015 Byrne et al.
PP28,077 P3 6/2017 Byrne et al.

OTHER PUBLICATIONS

U.S. Appl. No. 19/336,141, filed Sep. 22, 2025, Byrne et al.
U.S. Appl. No. 19/336,148, filed Sep. 22, 2025, Byrne et al.
U.S. Appl. No. 19/336,164, filed Sep. 22, 2025, Byrne et al.
U.S. Appl. No. 19/336,169, filed Sep. 22, 2025, Byrne et al.
U.S. Appl. No. 19/336,358, filed Sep. 22, 2025, Byrne et al.
U.S. Appl. No. 19/336,361, filed Sep. 22, 2025, Byrne et al.
U.S. Appl. No. 19/336,363, filed Sep. 22, 2025, Byrne et al.
U.S. Appl. No. 19/336,365, filed Sep. 22, 2025, Byrne et al.
U.S. Appl. No. 19/336,368, filed Sep. 22, 2025, Byrne et al.
U.S. Appl. No. 19/336,370, filed Sep. 22, 2025, Byrne et al.
U.S. Appl. No. 19/336,372, filed Sep. 22, 2025, Byrne et al.
U.S. Appl. No. 19/336,377, filed Sep. 22, 2025, Byrne et al.
U.S. Appl. No. 19/336,380, filed Sep. 22, 2025, Byrne et al.
U.S. Appl. No. 19/336,383, filed Sep. 22, 2025, Byrne et al.
U.S. Appl. No. 19/336,385, filed Sep. 22, 2025, Byrne et al.

*Primary Examiner* — Karen M Redden
(74) *Attorney, Agent, or Firm* — Dentons US LLP

(57) ABSTRACT

Disclosed is a new variety of *Prunus persica* named 'TRH1C104LW'. This new variety, which requires ~300 chilling units of dormancy, is considered to be a peach tree of early mid-season maturity, which produces white-fleshed, subacid fruit that are firm with a 60-80% red to maroon blush with a light-yellow to ivory ground color, and suitable for fresh fruit market use.

5 Drawing Sheets

Latin name of the genus and species of the plant claimed: *Prunus persica.*

Variety denomination: 'TRHIC104LW'.

CROSS-REFERENCE TO RELATED APPLICATIONS

Peach trees developed under the same breeding program as 'TRH1C104LW' include the co-pending applications listed below.

| U.S. application Ser. No. | Title |
|---|---|
| U.S. 19/336,141 | PEACH TREE NAMED 'TX3C490LWP' |
| U.S. 19/336,148 | PEACH TREE NAMED 'TRH2E68L' |
| U.S. 19/336,164 | PEACH TREE NAMED 'TRH3B53L' |
| U.S. 19/336,169 | PEACH TREE NAMED 'TRH3C114W' |
| U.S. 19/336,358 | PEACH TREE NAMED 'TRH2E121L' |
| U.S. 19/336,361 | PEACH TREE NAMED 'TRH3A17' |
| U.S. 19/336,363 | PEACH TREE NAMED 'TRH2E120LW' |
| U.S. 19/336,365 | PEACH TREE NAMED 'TRH3C113LW' |
| U.S. 19/336,368 | PEACH TREE NAMED 'TRH3E88LW' |
| U.S. 19/336,370 | PEACH TREE NAMED 'TX2B449LW' |
| U.S. 19/336,385 | PEACH TREE NAMED 'TRH2B102LW' |

-continued

| U.S. application Ser. No. | Title |
|---|---|
| U.S. 19/336,372 | PEACH TREE NAMED 'TX2C465CW' |
| U.S. 19/336,377 | PEACH TREE NAMED 'TRH3C111' |
| U.S. 19/336,380 | PEACH TREE NAMED 'TRH2C108W' |
| U.S. 19/336,383 | PEACH TREE NAMED 'TRH2E116L' |

BACKGROUND OF THE INVENTION

This invention relates to a peach tree and, more specifically, to a peach tree referred to as a variety of *Prunus persica* named 'TRH1C104LW', which requires approximately 300 chilling units of dormancy, produces a firm clingstone, white-fleshed, subacid peach with a 60-80% red to maroon blush with a light-yellow to ivory ground color that matures in the early mid-season. The present peach tree was the result of an ongoing Stone Fruit Breeding Program in College Station, Brazos County, Texas. To this end, controlled crosses were made each year to produce seedling populations from which improved progenies are evaluated and selected. The seedling 'TRH1C104LW' was derived from a population of seedlings derived by crossing the white-fleshed, subacid, nectarine 'Smooth Delight One' (patented, U.S. Plant Pat. No. 28,077) with the low-chill, acid-sweet, yellow-fleshed peach selection 'TX2B136' (not patented). 'TX2B136' was selected from a progeny created by crossing the low-chill, yellow-fleshed peach 'Hermosillo' (Sherman, W. B., J. Rodriguez-Alcazar, and B. L. Topp. 1992. Peaches and nectarines developed but not introduced by the University of Florida. Fruit Varieties Journal 46:124-127, not patented) and the low-chill, yellow-fleshed, peach selection 'TXW1293-1' (not patented). 'TXW1293-1' is a selection from a large open pollinated population derived from the variety 'Tropic Beauty' (Sherman, W. B. and R. E. Rouse. 1989. Five new low-chill peach cultivars. Fruit Varieties Journal 43:120, not patented). The seedlings from the hybrid population from the 'Smooth Delight One' x TX2B136 cross were planted in 2011 in an experimental plot in Floresville, TX. 'TRH1C104LW' was marked for subsequent observation in 2013 and noted as having exceptional characteristics.

'TRH1C104LW' was bud grafted onto virus-free 'Nemaguard' (not patented, The Brooks and Olmo Register of Fruit and Nut Varieties, 3rd Ed., American Society of Horticultural Science Press, Alexandria, VA, 1997) peach at the nursery site in Oakdale, CA. The variety was subsequently planted and evaluated as two-year and older trees in Pleasanton (2018-2023), and Somerville (2016-2020) Texas. This evaluation clearly demonstrated that the re-propagated trees were true to the characteristics of the original seedling in all observable aspects.

SUMMARY OF THE INVENTION

The 'TRH1C104LW' peach is characterized by producing clingstone, white-fleshed, subacid fruit that ripens in the early mid-season and produces a firm fruit with a 60-80% red to maroon blush with a light-yellow to ivory ground color. In this regard, the present variety of peach tree bears fruit that are ripe for commercial harvesting and shipment in late May, when the fruit is grown in the medium chill zone of Texas. 'TRH1C104LW' blooms 5 days before and ripens 2½ weeks after its female parent 'Smooth Delight One' (patented, U.S. Plant Pat. No. 28,077). 'TRH1C104LW' differs from its yellow-fleshed, acid-sweet, low chill peach female parent, 'TX2B136' (not patented), as it has subacid, white flesh and requires ~100 chill hours more to fruit. This new subacid, white-fleshed peach exhibits potential to be commercialized in regions that have chilling requirements that are low.

'TRH1C104LW' has showy versus non showy flowers, has reniform versus globose glands, blooms about 18 days earlier and ripens about 3 weeks later than the medium chill, white-fleshed, subacid peach cultivar 'White Delight One' (not patented, US App. Pub. No. 2016/2016/0205833 P1, abandoned). 'TRH1C104LW' has a showy flower versus a non showy flower, has reniform glands versus globose glands, blooms about 3 weeks earlier and ripens about 10 days earlier than 'White Delight Two' (not patented, US App. Pub. No. 2016/0205832 P1, abandoned). 'TRH1C104LW' has white versus yellow flesh, blooms about 4 days earlier and ripens about 1 week earlier than its sister seedling 'TRH2E116L' (U.S. Ser. No. 19/336,383). 'TRH1C104LW' has white flesh versus yellow flesh and ripens about one week earlier than 'TRH2E121L' (U.S. Ser. No. 19/336,358) and 'TRH3C111' (U.S. Ser. No. 19/336,377) which are derived from the reciprocal cross of the same parentage ('TX2B136' x 'Smooth Delight One').

BRIEF DESCRIPTION OF THE DRAWINGS

This new variety of peach tree is illustrated by the accompanying photographs of 3-year old plants grown in Somerville, Texas, as provided in FIGS. 1-5. These photographs show the plant's typical fruit, foliage, and flowers, and the colors shown are as true as can be reasonably obtained by conventional photographic procedures.

DETAILED BOTANICAL DESCRIPTION

Figure 1:
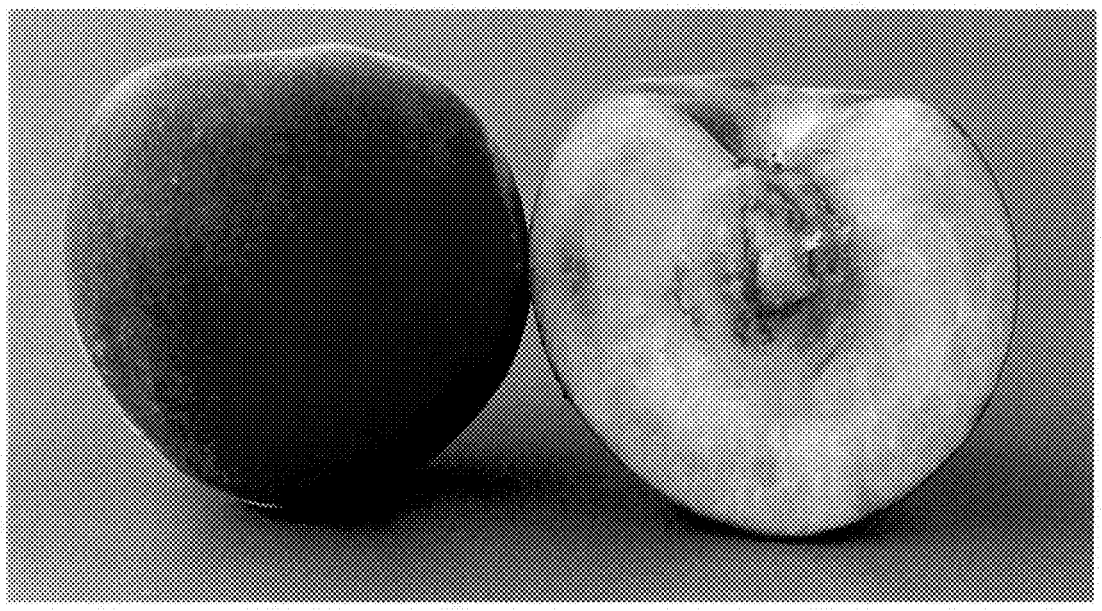
FIG. 1. Fruit of 'TRH1C104LW' produced in Somerville, Texas showing external and internal coloration.
Figure 2:
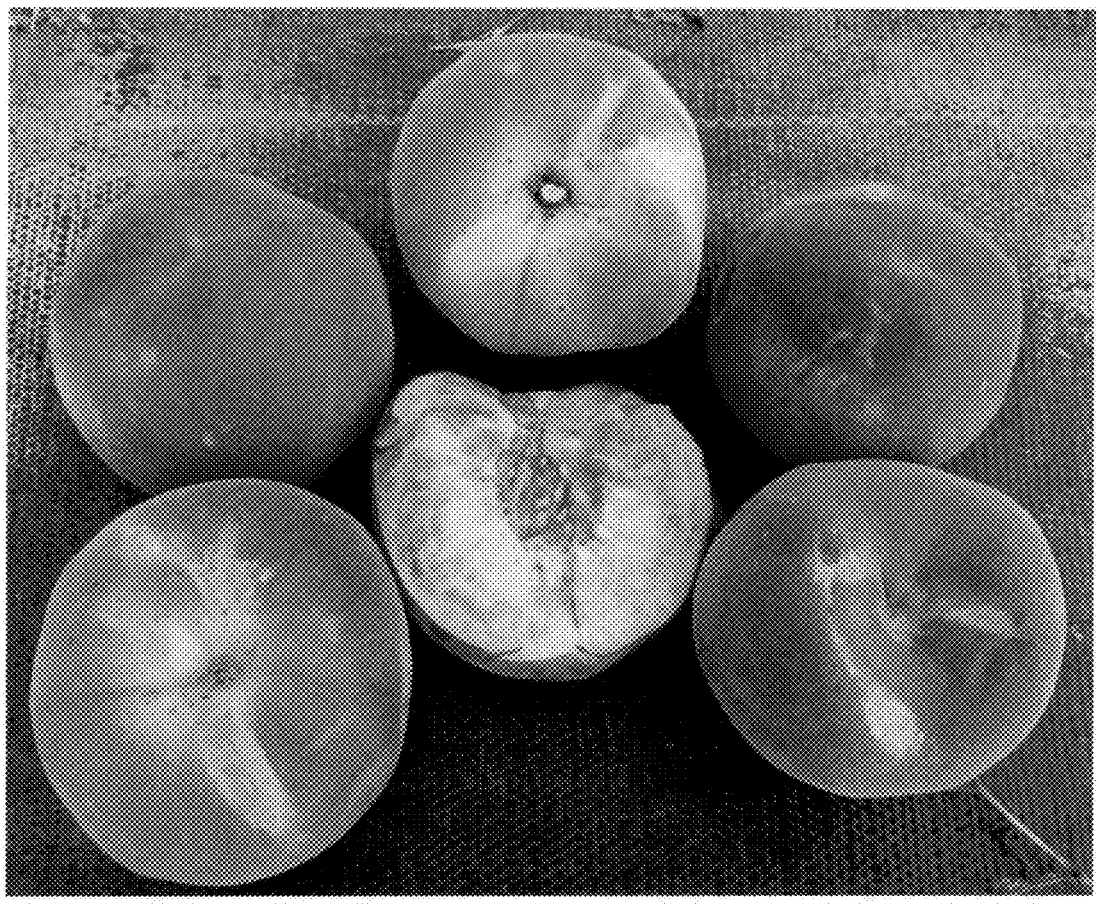
FIG. 2. 'TRH1C104LW' fruit produced in Somerville, Texas showing shape and external coloration.
Figure 3:
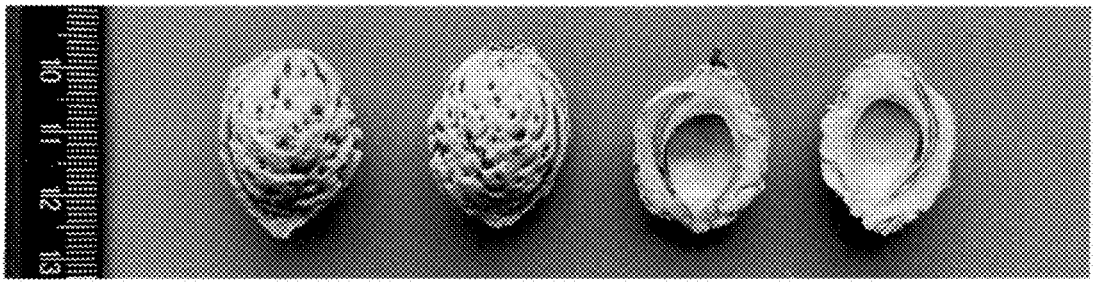
FIG. 3. Photograph of the endocarps of 'TRH1C104LW' peach. Ruler is in centimeters.
Figure 4:
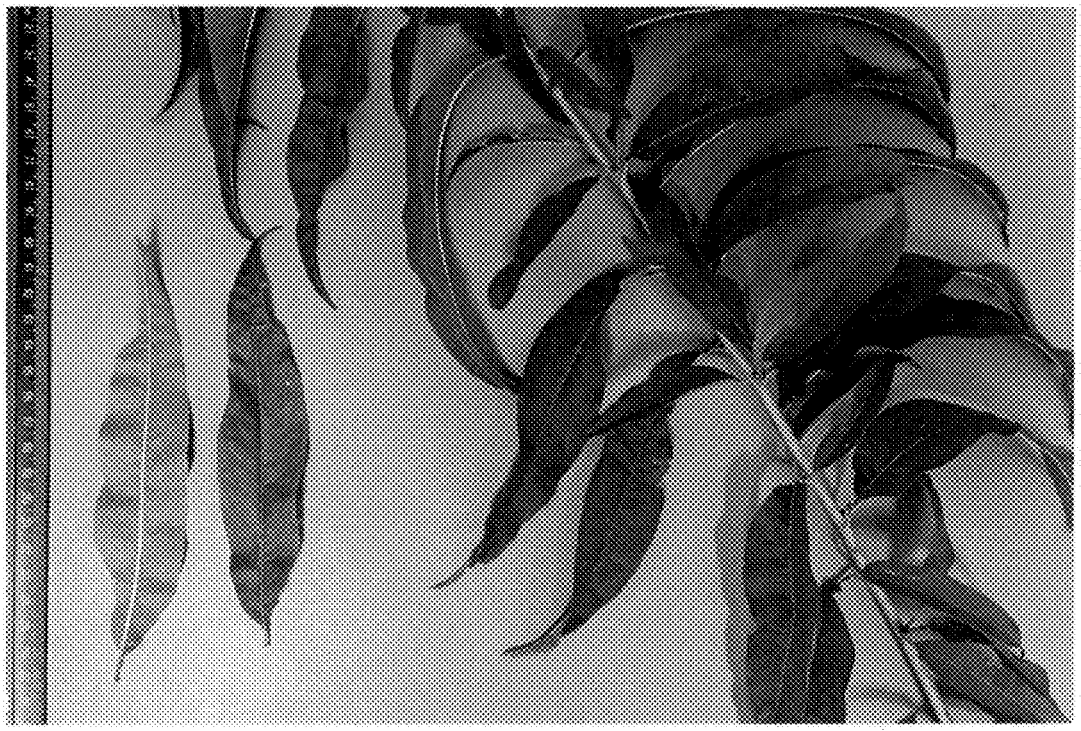
FIG. 4. A stem showing the leaves of 'TRH1C104LW' peach. Ruler is in centimeters FIG. 5. A stem showing the flowers of 'TRH1C104LW' peach. Ruler is in centimeters.
Figure 5:
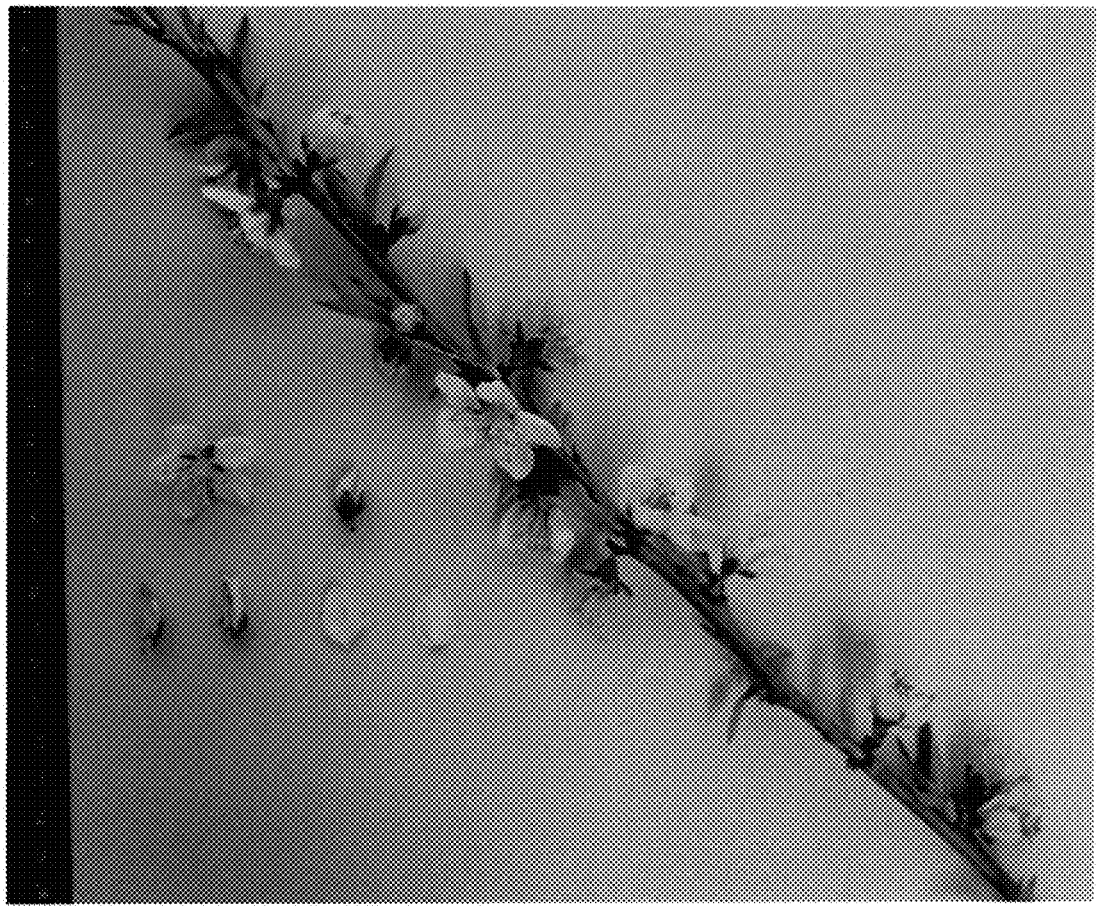

Referring more specifically to the pomological details of this new and distinct variety of peach tree, the following has been observed under the ecological conditions prevailing at the experimental orchards in the medium chill zone of Texas (Pleasanton and Somerville). All major color code designations are by reference to The R.H.S. Colour Chart (2001 Edition) provided by The Royal Horticultural Society of Great Britain. Colors are approximate as color depends on horticultural practices such as light level and fertilization rate, among others.

Tree:

*Size*.—Generally average as compared to other common peach cultivars ripening in the early season of maturity.

*Height*.—8 feet (2.4 m) at the end of the 2024 growing season.

*Width*.—8 feet width (2.4 m) at the end of the 2024 growing season.

*Productivity*.—Produces annually in the medium chill zone of Texas without alternate bearing if temperatures of 28° F. or lower are not experienced during bloom. Trees are self-fertile and must be fruit thinned most years to avoid limb breakage and obtain optimal fruit size. The recommended fruit spacing for early to mid-season ripening fresh market peach cultivars for a full crop is one fruit every 6-8" of one-year old fruiting wood. Trees often set more fruit than needed for a full crop.

*Shape*.—The 'TRH1C104LW' peach has been trained in an open center configuration but exhibits a semi spreading growth type as seen in peach varieties 'Texprince' (patented, U.S. Plant Pat. No. 14,629) and 'Texking' (patented, U.S. Plant Pat. No. 14,627).

*Current season growth*.—The current season growth for the new variety was approximately 1 to 3 feet (0.3-0.9 m). Vigor is medium compared to other common peach varieties grown in the medium chill zone of Texas.

*Regularity of bearing*.—Regular in the absence of temperatures of 28° F. or lower during bloom and considered hardy in the medium chill zone of Texas.

Trunk:

*Size*.—Approximately 2.75 inches (7.0 cm) in diameter and 9.75 inches (24.8 cm) in circumference when measured at a distance of approximately 12 inches (30.5 cm) above the soil level, at the end of the 2024 growing season on a three-year old tree.

*Bark texture*.—Considered moderately rough with numerous folds of papery scarf-like skin being present.

*Bark coloration*.—Variable, colors (RHS2001) present are 156A, 156B, 156C and 156D of the Greyed-White Group, 166A and 176A of the Greyed-Orange Group, 183A, 183B, and 183C of the Greyed-Purple Group, 196C and 196D of the Greyed-Green Group, N200D of the Brown Group and 202D of the Black Group.

Branches:

*Size*.—Considered medium for the species.

*Thickness*.—Average (about 3.5 cm in diameter as measured 10 cm from the trunk on a five-year old tree) as compared to other varieties.

*Surface texture*.—Average and appearing furrowed on wood that is several years old.

*Lenticels*.—Numerous flat, oval lenticels present. The lenticels range in size from approximately 5 to 11 mm in width and were approximately 1 to 2 mm in height.

*Current season shoots*.—Surface texture-Substantially glabrous.

*Internode length*.—Approximately 18 to 20 mm as measured in the middle of a current season stem.

*Color of mature branches*.—The predominant colors (RHS2001) are 166B, 172A, 172B, 173A, 75A, 75B and 177A of the Greyed-Orange Group, 197D and 198D of the Greyed-Green Group, 201D of the Grey Group and 202D of the Black Group.

Leaves:

*Size*.—Considered moderately large for the species. Leaf measurements have been taken from vigorous upright current season growth approximately at mid-shoot.

*Leaf length*.—Approximately 155 to 176 mm.

*Leaf width*.—Approximately 31 to 38 mm.

*Leaf thickness*.—Less than 1 mm.

*Leaf form*.—Lanceolate.

*Leaf tip form*.—Acuminate.

*Leaf upper surface color* (*RHS*2001).—Green varying among 146A and 147B of the Yellow-Green Group.

*Leaf lower surface color* (*RHS*2001).—Green varying among 138B of the Green Group and 147B of the Yellow-Green Group.

*Leaf lower mid-vein color*.—Light yellow green, 145C and 145D of the Yellow-Green Group.

*Leaf margins*.—Form — Considered crenate. Uniformity — Considered generally uniform.

*Leaf petioles*.—Length — Approximately 8 to 11 mm. Thickness — Approximately 1.5 mm. Texture — Glabrous. Color (RHS2001) — Pale green, approximately 143C of the Green Group, 144A, 144B, 146A, 146B, 146C and 147C of the Yellow-Green Group.

*Leaf glands*.—Size — Approximately 1 mm in height and less than 1 mm in width. Number — Generally 0-1 per leaf. Type — Reniform. Color (RHS2001) — Brown, approximately 177A of the Greyed-Orange Group and N199B of the Grey-Brown Group.

*Leaf stipules*.—The stipules are early deciduous and were not available for observation. Ratio of floral buds to vegetative buds-Generally 2 flower buds per vegetative bud Flowers:

*Floral buds*.—General — The floral buds are conic in form, and slightly appressed relative to the bearing shoot. Color (RHS2001) — The mature floral buds are brown, (approximately 165A, 166A and 166B of the Greyed-Orange Group and 200B and 200C of the Brown Group). Mature Bud Length — Approximately 5 to 6 mm. Mature Bud Width — Approximately 2 mm. Blooming Type — Mean date of full bloom in the medium chill zone of Texas was in early February (February 10$^{th}$ at Somerville), ~4 days after 'Texfirst' (Byrne, D. H. and N. Anderson. 2012. 'TexFirst', An early ripening low chill peach for the subtropics. HortScience 47:1803-1804. U.S. Plant Pat. No. 26,199, 24 Nov. 2015) and 7-12 days before the commercial cultivars 'Texking' and 'Flordaking' (not patented).

*Flower type*.—Showy.

*Flower size*.—Flower diameter at full bloom is approximately 33-40 mm.

*Bloom quantity*.—Considered abundant.

*Flower bud frequency*.—Generally 2 floral buds per node.

*Petal size*.—Width — Approximately 13 to 14 mm. Length — Approximately 21 to 22 mm. Petal Form — Broadly ovate. Petal Number — Nearly always 5.Petal Abaxial/adaxial Color (RHS2001) — Medum pink when young (56A, 56B, 56C and 56D of the Red Group and 62C, 63D, 65B, 65C, 65D, 69C and 69C of the Red-Purple), becoming darker near the petal claw.

*Petal claw*.—Form — The claw is considered truncate in shape. Length — Approximately 1-2 mm. Width — Approximately 1 mm.

*Petal margins*.—Generally considered variable, from nearly smooth to slightly undulate.

*Petal apex*.—Generally-The petal apices appear slightly rounded.

*Flower pedicel*.—Length — Average length of 5 mm. Thickness — Approximately 1 mm. Color (RHS2001) — A light green (144D, N144C, N144D of the Yellow-Green Group).

*Floral nectaries*.—Color (RHS2001) — Very light yellow (2A, 2B, 2C, 3A, 3B, 3C, 3D, 4A, 4B, 4C, 4D, 5A, 5B, 5C, 5D, 6A, 6B, 6C, 6D, 7D, 8B, 8C, 9C, 10B, 10C, 11A, 11B and 11C of the Yellow Group).

*Sepals*.—Sepal Number — Five per flower. Surface Texture — The surface has a short, fine, wooly texture. Size — Average Height 5.7 mm; Width 4.2 mm. Form — Ovate. Color (RHS2001) — Green with maroon (approximately 46A and 53A of the Red Group, 58A, 59A, 59B, 59C, 60A and 60B of the Red-Purple Group, 144B, N144C, N144D, 146C, 146D and 147D of the Yellow-Green Group, 183A, 183B, 183C, 184A, 184B, 185A, 185B and 187D of the Greyed-Purple Group).

*Floral cup* (*hypanthium*).—Surface Texture — Generally glabrous. Color (RHS2001) — Maroon (approximately 46A and 53A of the Red Group, 58A, 59A, 59B, 59C, 60A and 60B of the Red-Purple Group, 183A, 183B, 183C, 184A, 184B, 185A, 185B and 187D of the Greyed-Purple Group).

*Anthers*.—Color (RHS2001) — A very light yellow (approximately 2C, 2D, 3D, 4C, 4D, 5D, 6D, 8C, 8D, 9D, 10D, 11C and 11D of the Yellow Group).

*Pollen production*.—Pollen is abundant and is a golden yellow color (approximately 17A and 17B of the Yellow-Orange Group).

*Filaments*.—Size — Variable in length, approximately 9 to 16 mm, with the filaments being equal to the pistil and below the petal height. Color (RHS2001) — Very light pink (approximately 62D, 65D, 69A, 69B, 69C, 69D and 73D of the Red-Purple Group and N155B and N155C of the White) and darkening with advanced maturity.

*Pistil*.—General — Equal to the general anther height and below the petal height. Length — Approximately 14 to 17 mm, including the ovary. Color (RHS2001) — Considered a light yellow-green when young (approximately 1C and 1D of the Green-Yellow Group and 155A, 155B, 155C and 155D of the White Group) and becoming slightly darker with advancing senescence.

*Surface texture*.—The variety has a long, silver white pubescent pistil (approximately 155B and 155D of the White Group).

Fruit:

*Maturity when described*.—The present variety of fruit is described, as it would be found in its firm ripe condition at full commercial maturity. Under the ecological conditions prevailing in the medium chill zone of Texas it would be ripe in late May. The average ripe date in the Pleasanton and Somerville experimental plots was May 25$^{th}$ and May 27$^{th}$ respectively.

*Size*.—General-Medium large for the season and considered uniform. Average Cheek Diameter — Approximately 61 to 69 mm. Average Suture Diameter — Approximately 62 to 64 mm. Average Axial Diameter — Approximately 54 to 59 mm.

*Fruit form*.—Generally considered round to round ovate. Rarely, the fruit exhibits less symmetry when comparing the suture height with the line opposite the suture. The fruit is generally uniform in symmetry when viewed from the apical aspect.

*Fruit suture*.—Generally, the suture appears as a thin line that extends from the base to the apex, and appears deeper at the apex, forming a shallow basin at the apical point. No apparent callusing or stitching exists along the suture line. Fruit suture depth at the midpoint is less than 1 mm. Color (RHS2001) — Dark red to maroon. 46A, 53A and 53B of the Red Group and 60A and 69A of the Red-Purple Group.

*Ventral surface*.—Form-Considered uniform.

*Stem cavity*.—Width — Approximately 17 to 19 mm. Length — Approximately 21 to 24 mm. Depth — Approximately 8 to 10 mm.

*Fruit base*.—Considered flat.

*Fruit apex*.—Flat and round.

*Fruit stem*.—Length — 7 to 8 mm. Thickness — Approximately 3 mm. Color (RHS2001) — Light green, from 144D, 145B and 151D of the Yellow-Green Group.

*Fruit skin*.—Generally considered medium or average in thickness. Surface Texture — Light, short pubescence. Skin Acidity — Considered neutral. Tenacious to Flesh — Yes at commercial maturity. Tendency to Crack — Cracking not observed. Skin Color — Generally-Variable, with approximately 60-80% of the fruit surface covered with a marbled to solid medium red to maroon blush. Blush Color (RHS2001) — Medium red to maroon. 46A, 47A, 47B, 48A and 53A of the Red Group, 59A, 59B and 60A of the Red-Purple Group and 183A, 183B, 183C, 185A, 187B and 187C of the Greyed-Purple Group. Skin Ground Color (RHS2001) — Very light yellow to ivory. 1D of the Green-Yellow Group, 2D, 4D, 8C and 8D of the Yellow Group and 155A and 155C of the White Group.

*Flesh color* (*RHS*2001).—Ivory. 155A and 155C of the White Group. Anthocyanin coloration of the flesh is generally weak to medium next to the skin, centrally and next to the pit.

*Flesh fibers*.—Present throughout the flesh.

*Stone cavity color* (*RHS*2001).—Ivory with very light green. 155A and 155C of the White Group, 154D of the Yellow-Green Group and 157C and 157D of the Green-White Group.

*Flesh texture*.—Generally, the flesh is considered firm at commercial maturity.

*Ripening*.—Generally the fruit of the present variety ripens evenly.

*Flavor*.—Considered very sweet (Average 14.6 Brix) and rich, with subacid flavor.

Stone:

*Attachment*.—Clingstone at commercial maturity.

*Stone size*.—Generally considered medium to medium-large relative to the ratio of stone to fruit size. Length — Approximately 28 to 33 mm. Width — Approximately 21 to 22 mm. Thickness — Approximately 15 to 16 mm.

*Fibers*.—Generally a few medium length fibers are attached along the entire surface of the stone.

*Stone form*.—Elliptical.

*Stone base angle*.—Considered medium to wide.

*Hilum*.—Generally considered rather poorly defined as is common in early ripening varieties. The hilum is approximately 3 to 5 mm long and less than 1 mm wide.

*Stone apex angle*.—Medium.

*Stone shape*.—Normally ovoid to elongated.

*Stone surface*.—Surface Texture — Consists of single pits, rosettes of pits and chains of pits. Ridges — Numerous fine ridges are present basally and converge towards the base of the stone.

*Ventral edge*.—Medium.

*Dorsal edge*.—Shape-Grooved and having moderately rough edges.

*Stone color* (*RHS*2001).—The color of the dry stone is medium brown, 159A of the Orange-White Group, 161A of the Greyed-Yellow Group and 164B, 164C, 165C and 165D of the Greyed-Yellow Group. The color of the inside surface of the endocarp is primarily light to medium brown, 158A of the Yellow-White Group, 159A and 159B of the Orange-White Group and 164C, 164D and 165D of the Greyed-Orange Group.

*Tendency to split*.—Splitting is relatively uncommon.

*Kernel*.—The kernel fills the endocarp at harvest and measures approximately 5-6 mm in thickness, 9-10 mm in width, and 14-15 mm in length. The colors (RHS2001) of the fresh kernels are light yellow to ivory, 4D, 5D, 8C, 8D, 9D, 10D, 11C, 12D and 13D of the Yellow Group, 14D, 15D, 16D, 18B, 18C and 18D of the Yellow-Orange Group, 155B of the White Group and 158B, 158C, and 158D of the Yellow-White Group. When dried the shriveled kernels measure approximately 2-2.5 mm in thickness, 9 mm in width, and 13-14 mm in length. The colors of the shriveled kernels are tan, primarily 18A, 18B and 18C of the Yellow-Orange Group, 158A of the Yellow-White Group and 161B, 161C and 161D of the Greyed-Yellow Group.

*Use*.—The subject variety, 'TRH1C104LW', is considered to be a peach tree requiring about 300 chill hours and of early-season maturity, which produces subacid, white-fleshed fruit which are firm with a 60-80% red to maroon blush over a light yellow to ivory ground color and which are useful for the fresh fruit market.

*Keeping quality*.—Average. Retains firmness and flavor after 14 days of refrigeration at 3-5° C.

*Resistance to insects and disease*.—Moderately susceptible to bacterial leaf spot (*Xanthomonas campestris* cv. *pruni*) as is the cultivar 'TexKing'. Otherwise, no atypical resistances/susceptibilities were noted under normal cultural practices to date.

*Shipping quality*.—Average. Fruit does not develop internal breakdown and retains good firmness and eating quality after 14 days of refrigeration at 3-5° C.

Although the new variety of peach tree possesses the described characteristics when grown under the ecological conditions prevailing in the medium chill zone of Texas in Somerville and Pleasanton, it will be understood that variations of the usual magnitude and characteristics incident to the changes in growing conditions, fertilization, pruning, and pest control are to be expected.

What is claimed is:

1. A new and distinct variety of peach tree named 'TRHIC104LW', as illustrated and described herein.

* * * * *